United States Patent [19]

Jackson

[11] 4,178,735
[45] Dec. 18, 1979

[54] METHOD OF SHEATHING CATHETER

[75] Inventor: Knute D. Jackson, McHenry, Ill.

[73] Assignee: The Kendall Company, Boston, Mass.

[21] Appl. No.: 815,120

[22] Filed: Jul. 13, 1977

[51] Int. Cl.² .......................... A61M 25/00; B65B 5/04
[52] U.S. Cl. ........................................... 53/473; 53/459;
128/349 R; 29/433; 206/363
[58] Field of Search ........ 128/349 R, 349 B, 349 BV,
128/348; 206/363, 364, 438, 443, 306; 229/87.2;
53/459, 473; 29/433

[56] References Cited

U.S. PATENT DOCUMENTS

| | | | |
|---|---|---|---|
| 3,112,031 | 11/1963 | Stewart | 128/349 R |
| 3,347,450 | 10/1967 | Godwin | 229/87.2 |
| 3,749,237 | 7/1973 | Dorton | 206/438 |
| 3,750,875 | 8/1973 | Juster | 128/349 R X |
| 3,934,721 | 1/1976 | Juster et al. | 128/349 R X |
| 3,967,726 | 7/1976 | Roeser | 206/306 |

*Primary Examiner*—Dalton L. Truluck
*Attorney, Agent, or Firm*—Powell L. Sprunger

[57] ABSTRACT

A catheter having an elongated folded sleeve of flexible material closely received on a shaft of the catheter. A method is provided for placement of the sleeve on the catheter shaft.

4 Claims, 7 Drawing Figures

U.S. Patent    Dec. 18, 1979    4,178,735
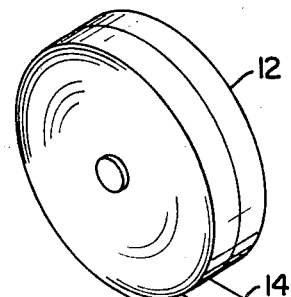
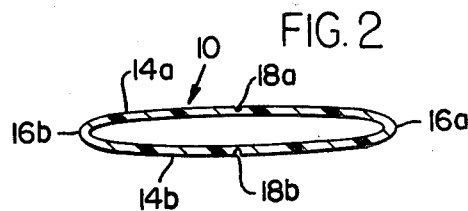
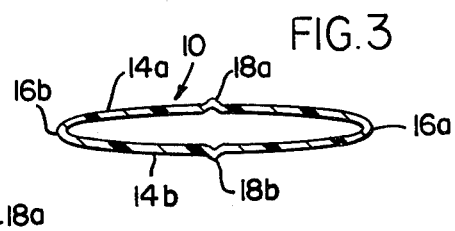
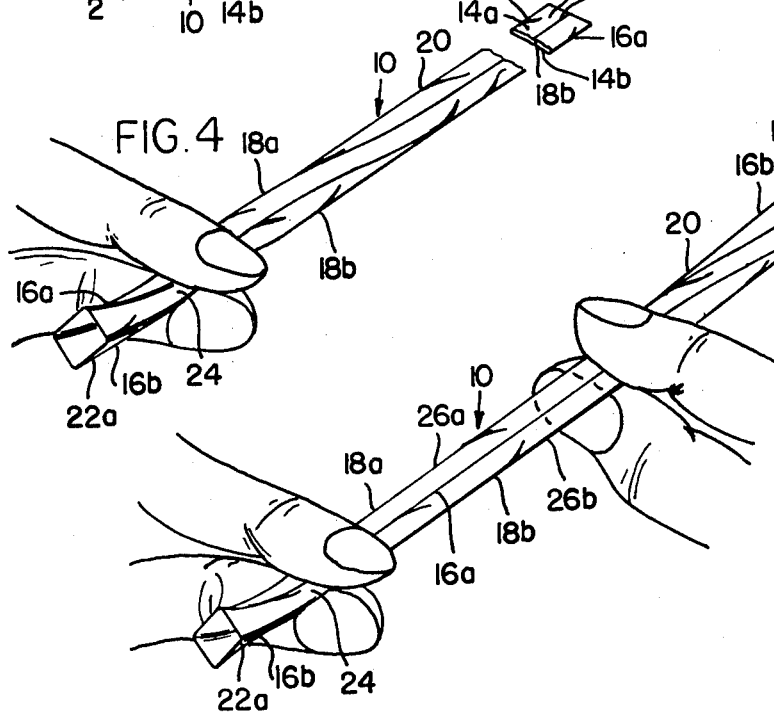
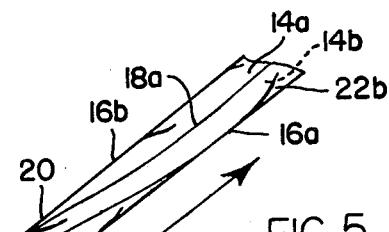
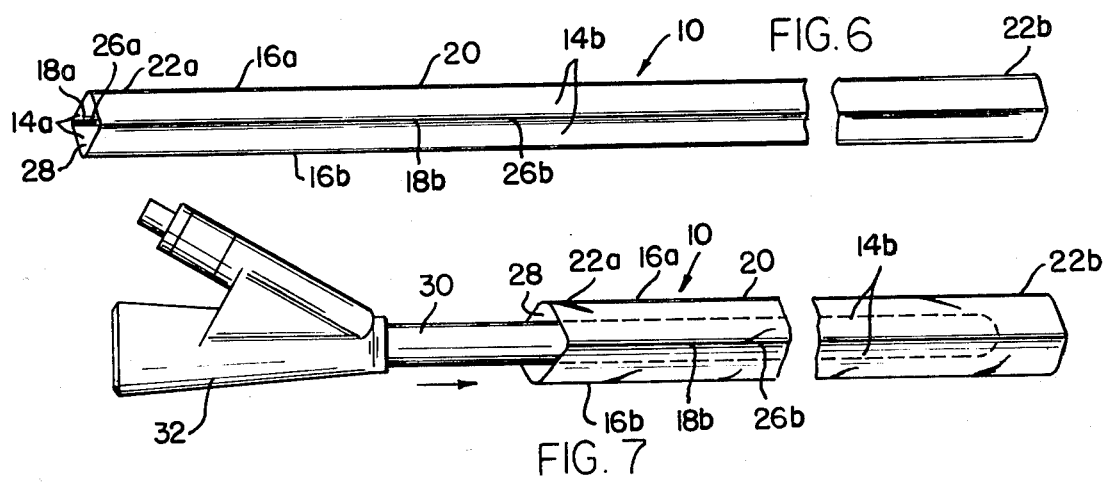

METHOD OF SHEATHING CATHETER

BACKGROUND OF THE INVENTION

The present invention relates to catheter assemblies, and more particularly to protective coverings for catheters.

An assortment of catheters have been proposed in the past for use on patients. In most cases such catheters must be available in a sterile condition at the time of use, and, accordingly, they are placed in suitable packages which are subjected to sterilization procedures in order to render the packaged catheter aseptic. In addition, it is desirable to further protect the shafts of certain catheters, such as Foley or urinary catheters, in the package. This follows since such catheters may develop static electricity and their shafts may attract lint or dust when the package is opened at the time of use, and since it is desirable to protect the catheter shafts from contamination during handling.

It would thus be desirable to place a sheath or sleeve of plastic material over the catheter shaft in order to accomplish this purpose. However, such a procedure has been found to be very difficult in practice, since the usual material of the sleeves provides an undue amount of friction and resistance against placement of the usual catheter shaft between the closely spaced walls of the sleeve, e.g. a sleeve made from a low density polyethylene and a catheter made from latex or a silicone material. Normally, placement of such a sleeve over the catheter shaft has been carried out by hand, and it has been found extremely difficult to insert such a catheter shaft into a sleeve which would fit relatively snugly about the shaft. Accordingly, it has been found necessary to use sleeves which have an unduly large size relative the diameter of the catheter shaft, although the covering procedure is still tedious when attempted without the aid of accessory devices, such as blowing machines to open the sleeves.

SUMMARY OF THE INVENTION

A principal feature of the present invention is the provision of an improved catheter assembly which may be formed in a simplified manner.

The catheter assembly of the invention comprises, a sleeve of flexible material received on the shaft. The sleeve has first and second walls extending between a pair of opposed first longitudinal folds, with each of the first and second walls having a longitudinal second fold located intermediate the first folds.

A feature of the invention is that the sleeve has inner dimensions slightly larger than the outer dimensions of the catheter shaft, such that the shaft is relatively snugly received within the sleeve.

Another feature of the invention is that the first and second walls are creased along longitudinally extending first and second lines in order to modify the sleeve from a generally flat to an open configuration.

A further feature of the invention is that the catheter shaft may be readily inserted into the sleeve while in the open configuration.

Still another feature of the invention is that in a preferred form the first and second lines may be located along lines of weakness in the first and second walls, such that the walls may be readily folded along the lines during placement of the catheter.

Yet another feature of the invention is that the sleeve may be twisted slightly to place the lines in the twisted portion at opposed sides of the sleeve and to facilitate folding of the sleeve along the lines.

Further features will become more fully apparent in the following description of the embodiments of this invention and from the appended claims.

DESCRIPTION OF THE DRAWINGS

In the drawings:

FIG. 1 is a perspective view of a roll of an elongated sleeve in a generally flat configuration;

FIG. 2 is a sectional view taken substantially as indicated along the line 2—2 of FIG. 1;

FIG. 3 is a sectional view of another embodiment of the sleeve for use in placement over a catheter shaft according to a method of the present invention;

FIG. 4 is a fragmentary perspective view of a sleeve being twisted in a portion according to a method of the present invention;

FIG. 5 is a perspective view of the sleeve as being folded along longitudinal lines according to a method of the present invention;

FIG. 6 is a fragmentary perspective view of the sleeve after a folding operation according to the present invention; and FIG. 7 is a fragmentary perspective view illustrating a catheter shaft as partially inserted into the folded sleeve.

DESCRIPTION OF THE PREFERRED EMBODIMENTS

Referring now to FIGS. 1 and 2, there is shown an elongated sleeve generally designated 10 of flexible material as wound into the configuration of a roll 12. The sleeve or shield 10 may be made of any suitable material, such as low or high density polyethylene, and in a preferred form is transparent. As shown, the sleeve 10 maintains a generally flat configuration when unwound from the roll 12, and has a pair of closely spaced opposed first and second walls 14a and 14b, respectively, extending between a pair of opposed longitudinal fold lines 16a and 16b, respectively, which connect the walls 14a and b. The walls 14a and b have longitudinal lines of weakness 18a and 18b, respectively, with the weakness lines 18a and b being generally aligned and located generally centrally intermediate the opposed folds 16a and b. In a suitable form, the weakness lines 18a and b may comprise longitudinal lines of reduced thickness in the walls 14a and b which may also serve as rupture or tear lines for the sleeve 10 during use. In an alternative form, as shown in FIG. 3, the weakness lines 18a and b may comprise pre-folds of the walls along fold lines 18a and b which extend longitudinally in the sleeve 10. If desired, the sleeve 10 may have lines of reduced thickness coinciding with the fold lines 16a and b at the edges of the sleeve. As will be seen below, the width of the walls 14a and b between the fold lines 16a and b is selected such that the sleeve 10 closely fits an associated catheter shaft when the sleeve covers the shaft, i.e., the placed sleeve 10 has inner dimensions slightly larger than the outer dimensions or diameter of the catheter shaft.

The sleeve 10 may be placed on the catheter shaft according to a method of the present invention which is described as follows. With reference to FIGS. 1 and 4, an end portion of the sleeve 10 may be unwound from the roll 12, and a segment 20 having end portions 22a and 22b and a length approximately equal to the length of the catheter shaft may be severed from the roll. With reference to FIG. 4, an end portion 24 of the sleeve 10 may be twisted slightly in order to position the lines of weakness 18a and b in the twisted portion 24 at the sides of the sleeve 10. Next, with reference to FIG. 5, the portion 24 of the sleeve 10 is retained by the fingers in the twisted configuration while the remainder of the sleeve 10 is creased or folded along the length of the weakness lines 18a and b intermediate the twisted portion 24 and the opposed sleeve ends 22a and b. After the folding operation has been completed the sleeve may be released, and the creases or fold lines along the weakness lines 18a and b, in addition to fold lines 16a and b, cause the sleeve walls to become separated. Thus, as shown in FIG. 6, the sleeve 10 assumes an open configuration and defines a cavity 28 of generally square cross-sectional shape between the sleeve walls 14a and b. Finally, with reference to FIG. 7, the shaft 30 of a catheter 32, such as a Foley catheter which may be made of latex or a silicone material, may be readily inserted into the cavity 28 of the creased sleeve 10 while the sleeve 10 is in the open configuration.

In accordance with the present invention, the sleeve 10 is creased along the weakness lines 18a and 18b in order to transform the sleeve from a generally flat to an open configuration, after which the catheter shaft 30 may be inserted into the cavity 28 of the folded sleeve 10. The sleeve may be readily placed on a catheter shaft having outer dimensions slightly less than the inner dimensions of the sleeve, e.g., a sleeve 10 having a width between folds 16a and b of approximately ⅜ inches may be easily placed on a catheter shaft having a diameter of approximately ¼ inches when carried out according to the method of the present invention, thus permitting simplified covering of a catheter shaft by a relatively snug sleeve which would otherwise be extremely difficult. The covered catheter may then be placed in a suitable package which is sterilized preparatory to use. After the package has been opened at the time of use, the sleeve 10 protects the catheter shaft from contamination during handling, and prevents the accumulation of dust or lint on the shaft in the event that the catheter should develop static electricity.

The foregoing detailed description is given for clearness of understanding only, and no unnecessary limitations should be understood therefrom, as modifications will be obvious to those skilled in the art.

I claim:

1. A method of covering an elongated limp cylindrical catheter shaft of generally uniform diameter with an elongated sleeve of non-rigid flexible plastic material having opposed first and second walls extending between a pair of opposed folds defining a generally flat configuration of the sleeve, and having a high coefficient of friction relative to the catheter shaft, comprising the steps of:

creasing said first and second walls along longitudinally extending first and second lines respectively located in said first and second walls generally centrally between said opposed folds while modifying the sleeve from said generally flat to an open configuration of square cross section having inner side dimensions slightly larger than the diameter of said catheter shaft to facilitate insertion of said catheter shaft into said sleeve; and inserting the catheter shaft between the walls of the sleeve while in said open configuration.

2. The method of claim 1 wherein said creasing step comprises the step of folding said first and second walls along lines of weakness in said walls.

3. The method of claim 1 wherein said creasing step comprises the step of folding said first and second walls along fold lines pre-folded in said walls.

4. The method of claim 1 including the step of twisting a portion of said sleeve sufficiently to place said lines at opposed edges of the sleeve in said twisted portion.

* * * * *